(12) United States Patent
Reichl

(10) Patent No.: US 11,071,813 B2
(45) Date of Patent: Jul. 27, 2021

(54) EXTRACORPOREAL BLOOD HEATING AND COOLING SYSTEM AND METHOD OF OPERATING AND MAINTAINING SAME

(71) Applicant: Maquet Cardiopulmonary GmbH, Rastatt (DE)

(72) Inventor: Herwig Ernst Reichl, Ilz (AT)

(73) Assignee: MAQUET CARDIOPULMONARY GMBH, Rastatt (DE)

( * ) Notice: Subject to any disclaimer, the term of this patent is extended or adjusted under 35 U.S.C. 154(b) by 341 days.

(21) Appl. No.: 16/179,624

(22) Filed: Nov. 2, 2018

(65) Prior Publication Data
US 2019/0134294 A1 May 9, 2019

Related U.S. Application Data

(60) Provisional application No. 62/582,300, filed on Nov. 6, 2017.

(51) Int. Cl.
*A61M 1/36* (2006.01)
*A61M 1/16* (2006.01)
*A61M 1/32* (2006.01)

(52) U.S. Cl.
CPC .......... *A61M 1/3664* (2013.01); *A61M 1/169* (2013.01); *A61M 1/32* (2013.01);
(Continued)

(58) Field of Classification Search
CPC .... A61M 1/3664; A61M 1/32; A61M 1/3666; A61M 1/1629; A61M 1/1698;
(Continued)

(56) References Cited

U.S. PATENT DOCUMENTS 5,645,531 A * 7/1997 Thompson .............. A61M 5/44
604/67
6,423,268 B1 7/2002 King et al.
(Continued)

FOREIGN PATENT DOCUMENTS

WO 01/19414 A1 3/2001

OTHER PUBLICATIONS

International Preliminary Report on Patentability issued in counterpart International Application No. PCT/EP2018/080054, dated May 22, 2020. (11 pages).
(Continued)

*Primary Examiner* — Ariana Zimbouski
(74) *Attorney, Agent, or Firm* — Kevin T. Godlewski

(57) ABSTRACT

An extracorporeal blood heating and cooling system that is connectable to an oxygenator of a cardiopulmonary bypass system, the heating and cooling system comprising: a heater-cooler unit; a coolant flow circuit that is configured to pass coolant through the heater-cooler unit and the oxygenator; and a cardioplegia coolant circuit that is configured to pass coolant through the heater-cooler unit and a cardioplegia heat exchanger; wherein when the heating and cooling system is in a purging mode, the coolant flow circuit and the cardioplegia coolant circuit contain temperature-controlled coolant having a trisodium phosphate concentration of about 1-35 millimole/liter; wherein when the heating and cooling system is in a coolant mode, the coolant flow circuit and the cardioplegia coolant circuit contain temperature-controlled coolant having a trisodium phosphate concentration of about 1-10 millimole/liter; and wherein when the heating and cooling system is in the coolant mode or the purging mode, a first and second plurality of coolant conduits within the oxygenator and the cardioplegia heat exchanger are capable of maintaining a trisodium phosphate concentration ratio
(Continued)

across the wall of such coolant conduits of at least 100:1, from the interior to the exterior of each coolant conduit. Methods of purging and operating such extracorporeal blood heating and cooling systems are also disclosed.

24 Claims, 3 Drawing Sheets

(52) U.S. Cl.
CPC ......... *A61M 1/3666* (2013.01); *A61M 1/1629* (2014.02); *A61M 1/1698* (2013.01); *A61M 2202/0472* (2013.01); *A61M 2205/0205* (2013.01); *A61M 2205/025* (2013.01); *A61M 2205/3368* (2013.01); *A61M 2205/36* (2013.01); *A61M 2205/366* (2013.01); *A61M 2205/3606* (2013.01)

(58) Field of Classification Search
CPC ...... A61M 2205/36; A61M 2205/3368; A61M 2205/3606; A61M 2205/366
See application file for complete search history.

(56) References Cited

U.S. PATENT DOCUMENTS

| | | | |
|---|---|---|---|
| 6,702,773 B1* | 3/2004 | Macoviak | A61M 1/3653 604/4.01 |
| 2008/0027368 A1 | 1/2008 | Kollar et al. | |
| 2008/0027638 A1 | 1/2008 | Kollar et al. | |
| 2008/0031773 A1* | 2/2008 | Eccleston | A61M 1/3666 422/44 |

OTHER PUBLICATIONS

International Search Report and Written Opinion dated Jan. 29, 2019 which issued for corresponding international application No. PCT/EP2018/080054, 18 pages.
Dissertation of Christian Kuhn (with English machine-translation of Abstract), 2013, 218 pages.
Maquet Getinge Group, Field Safety Corrective Action (FSCA), Use of Hydrogen Peroxide in Heater-Cooler Systems with Maquet Oxygenators, Dec. 19, 2015, 6 pages.

* cited by examiner

EXTRACORPOREAL BLOOD HEATING AND COOLING SYSTEM AND METHOD OF OPERATING AND MAINTAINING SAME

CROSS-REFERENCE TO RELATED APPLICATION

This application claims the benefit of U.S. Provisional Application No. 62/582,300, filed on Nov. 6, 2017, which is incorporated herein by reference in its entirety.

FIELD OF THE DISCLOSURE

The field of the present disclosure pertains to that of extracorporeal blood heating and cooling systems and methods of operating and maintaining such systems, particularly those relating to cardiopulmonary bypass systems and procedures. More specifically, the present disclosure pertains to extracorporeal blood heating and cooling systems that manage the quality of the coolant by utilizing an additive to maintain the system's coolant circuits by creating a microbial impeding environment. A cardiopulmonary bypass system in accordance with this disclosure includes heart-lung machines, extracorporeal membrane oxygenation (ECMO) apparatuses, and pump assisted lung protection (PALP) apparatuses.

BACKGROUND OF THE DISCLOSURE

During cardiac surgery, heater-cooler units are used to control the patient's body temperature by means of heating and/or cooling the blood flow of an extracorporeal blood circuit and to apply thermal cardioplegia. Heater-cooler units include tanks containing temperature-controlled water that is provided to external heat exchangers or to warming/cooling blankets through closed water circuits. Because the water circuits are closed, the water in the circuits and the heater-cooler units does not come in contact with the blood of the patient.

Heater-cooler units and heater units are used in sensitive sterile environments, such as operation theatres. During cardiovascular procedures in on-pump cardiac surgery, the heater-cooler unit is applied to cool down a patient during an intervention (in order to reduce the metabolic rate and oxygen consumption for organ protection), to warm up the patient to a physiological temperature when the intervention is completed, as well as to keep a favored temperature constant during cardiopulmonary bypass surgery. The temperature transfer occurs via a heat exchanger in the coolant flow circuit and/or in the cardioplegia water circuit, and/or via a warming/cooling blanket.

Some heater-cooler units have been shown to harbor and spread germs (microbes), especially mycobacteria, which can lead to fatal infections. The traditional use of disinfection cycles, wherein the units are taken off line and their plumbing (including connecting tubes to the cardioplegia heat exchanger and/or oxygenator and the water pathways through the cardioplegia heat exchanger and/or oxygenator) are filled with disinfectants to reduce the number of microbes in the units, has several disadvantages. The disinfection cycles interrupt the use of the unit, often employ hazardous chemicals requiring safety precautions, and flushing the units before use is both time-and water-consuming. In addition, conventional disinfectants are often incompatible with the materials used in the units. For example, hydrogen peroxide has been used as a disinfectant for certain heater-cooler units; however, it is not a suitable disinfectant/bactericidal/bacteriostatic substance for other heater-coolant units. In some heater-cooler units, such as those that employ polyurethane conduits for carrying the coolant solution, it has been discovered by researchers in the field that hydrogen peroxide diffuses through the polyurethane material of the conduits employed in the heat exchanger when transporting temperature-controlled water in the coolant flow circuit and/or in the cardioplegia water circuit. As a result, the hydrogen peroxide is able to cross through the polyurethane material of the coolant conduits and come into contact with the blood of the patient carried in separate blood passages, which potentially leads to unsafe levels of hydrogen peroxide in the blood of the patient.

In addition, recovery and multiplication of surviving microbes shortly after the end of a disinfection cycle with conventional disinfectants is common, which necessitates regular (e.g., weekly) disinfection cycles be performed. With conventional disinfection cycles, increases in bacterial counts can be seen three days after termination of the disinfection cycle.

Thus, there is a need in the art for improved systems and methods for operating and maintaining heater-cooler units in a way that will create a microbial impeding environment for microbial populations, such as bio-films, spore-producing bacteria, yeasts and fungi, and other microbes. There is a further need for improved systems and methods for operating and maintaining these heater-cooler units such that any additive to the temperature-controlled coolant will be less likely to diffuse through the coolant conduits of the heat exchangers and come into contact with the blood of the patient. There is also a need for improved systems and methods for operating and maintaining these heater-cooler units that will reduce the number of required servicing cycles for the units and improve safety and user friendliness for the customer.

SUMMARY OF THE DISCLOSURE

A non-limiting system is disclosed herein that constitutes an extracorporeal blood heating and cooling system. In accordance with a non-limiting illustrative embodiment of such a system, an extracorporeal blood heating and cooling system that is connectable to an oxygenator of a cardiopulmonary bypass system is described that includes (a) a heater-cooler unit; (b) a coolant flow circuit that is configured to pass coolant through the heater-cooler unit and the oxygenator; and (c) a cardioplegia coolant circuit that is configured to pass coolant through the heater-cooler unit and a cardioplegia heat exchanger; wherein the oxygenator comprises a first plurality of coolant conduits that form part of the coolant flow circuit, and wherein when the heating and cooling system is in a coolant mode, blood passing through a first extracorporeal blood circuit contacts an exterior surface of the first plurality of coolant conduits; and wherein the cardioplegia heat exchanger comprises a second plurality of coolant conduits that are part of the cardioplegia coolant circuit, and wherein when the heating and cooling system is in the coolant mode, blood passing through a second extracorporeal blood circuit contacts an exterior surface of the second plurality of coolant conduits. In accordance with this non-limiting embodiment of the system, when the system is in a purging mode, the coolant flow circuit and the cardioplegia coolant circuit contain temperature-controlled coolant having a trisodium phosphate concentration of about 1-35 millimole/liter; when the system is in the coolant mode, the coolant flow circuit and the cardioplegia coolant circuit contain temperature-controlled coolant having a trisodium phosphate concentration of about 1-10 millimole/liter; and when the system is in the coolant mode or the purging mode, the first and second plurality of coolant conduits are capable of maintaining a trisodium phosphate concentration ratio across the wall of each coolant conduit of at least 100:1, from the interior to the exterior of each coolant conduit. Various other non-limiting illustrative embodiments of the system are also disclosed herein.

A method is disclosed herein that constitutes a method of purging an extracorporeal blood heating and cooling system that is connectable to an oxygenator of a cardiopulmonary bypass system, the heating and cooling system comprising: a heater-cooler unit; a coolant flow circuit that is configured to pass temperature-controlled coolant through the heater-cooler unit and an oxygenator; and a cardioplegia coolant circuit that is configured to pass temperature-controlled coolant through the heater-cooler unit and a cardioplegia heat exchanger; wherein the oxygenator comprises a first plurality of coolant conduits that form part of the coolant flow circuit when the oxygenator is connected to the heating and cooling system, and wherein when the heating and cooling system is in a coolant mode, blood passing through a first extracorporeal blood circuit contacts an exterior surface of the first plurality of coolant conduits; and wherein the cardioplegia heat exchanger comprises a second plurality of coolant conduits that are part of the cardioplegia coolant circuit, and wherein when the heating and cooling system is in the coolant mode, blood passing through a second extracorporeal blood circuit contacts an exterior surface of the second plurality of coolant conduits. Such a non-limiting illustrative embodiment of such a method comprises the steps of: adding temperature-controlled coolant to at least one of the coolant flow circuit or the cardioplegia coolant circuit, wherein the temperature-controlled coolant has a trisodium phosphate concentration of about 1-35 millimole/liter; and subsequently flowing the temperature-controlled coolant within the coolant flow circuit and/or the cardioplegia coolant circuit in a manner that at least inhibits growth of microbes within the coolant flow circuit and/or the cardioplegia coolant circuit; wherein the first and second plurality of coolant conduits are capable of maintaining a trisodium phosphate concentration ratio across the wall of each coolant conduit of at least 100:1, from the interior to the exterior of each coolant conduit. Various other non-limiting embodiments of this method are also disclosed herein.

A method is disclosed herein that constitutes a method of operating an extracorporeal blood heating and cooling system, wherein the heating and cooling system is connectable to an oxygenator of a cardiopulmonary bypass system, the heating and cooling system comprising: a heater-cooler unit; a coolant flow circuit that is configured to pass temperature-controlled coolant through the heater-cooler unit and the oxygenator; and a cardioplegia coolant circuit that is configured to pass temperature-controlled coolant through the heater-cooler unit and a cardioplegia heat exchanger; wherein the oxygenator comprises a first plurality of coolant conduits that form part of the coolant flow circuit when the heating and cooling system is connected to the oxygenator, and wherein when the heating and cooling system is operating in a coolant mode, blood passing through a first extracorporeal blood circuit contacts an exterior surface of the first plurality of coolant conduits; and wherein the cardioplegia heat exchanger comprises a second plurality of coolant conduits that are part of the cardioplegia coolant circuit, and wherein when the heating and cooling system is operating in the coolant mode, blood passing through a second extracorporeal blood circuit contacts an exterior surface of the second plurality of coolant conduits.

A non-limiting illustrative embodiment of such a method comprises the steps of: adding temperature-controlled coolant to the coolant flow circuit and the cardioplegia coolant circuit, wherein the temperature-controlled coolant has a trisodium phosphate concentration of about 1-10 millimole/liter and a pH of 10-13; and subsequently flowing the temperature-controlled coolant through the coolant flow circuit and the cardioplegia circuit in order to at least inhibit growth of microbes within the coolant flow circuit and the cardioplegia circuit; wherein the first and second plurality of coolant conduits are capable of maintaining a trisodium phosphate concentration ratio across the wall of each coolant conduit of at least 100:1, from the interior to the exterior of each coolant conduit. Various other non-limiting embodiments of this method are also disclosed herein.

DETAILED DESCRIPTION OF ILLUSTRATIVE, NON-LIMITING INVENTIVE EMBODIMENTS

Various illustrative, non-limiting embodiments of this disclosure are described as follows with reference to the drawings, in which like parts are designated with like character references.

Figure 1:
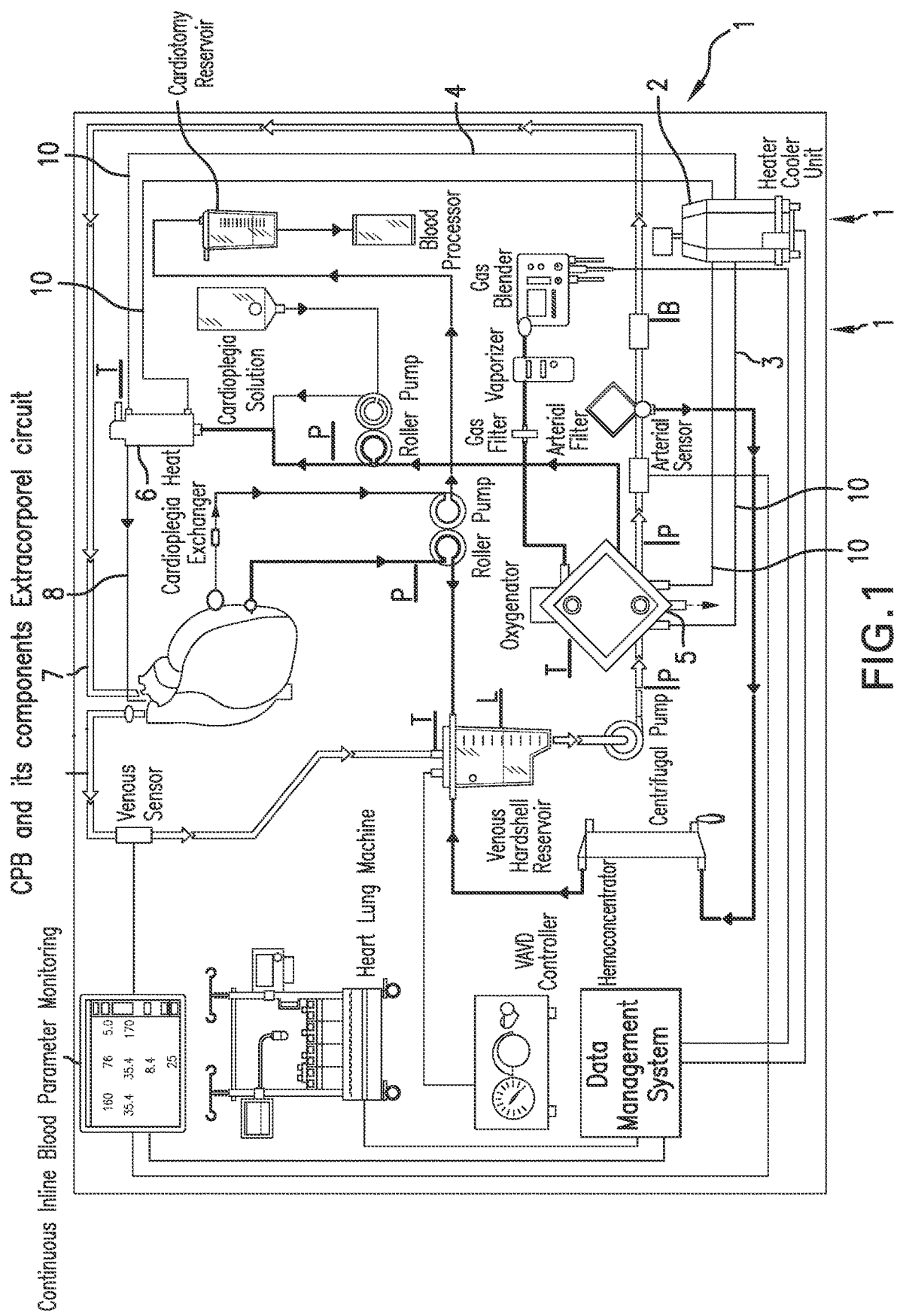
FIG. 1 is a schematic illustration of a cardiopulmonary bypass system, including a schematic illustration of an extracorporeal blood heating and cooling system in accordance with a non-limiting illustrative inventive embodiment of the present disclosure.

FIG. 1 shows an extracorporeal blood heating and cooling system 1, including a heater-cooler unit 2, a coolant flow circuit 3, and a cardioplegia coolant circuit 4. The heating and cooling system 1 is connectable to an oxygenator 5 and a cardioplegia heat exchanger 6 of a cardiopulmonary bypass system. The coolant flow circuit 3 and the cardioplegia coolant circuit 4 include pipes and/or tubes 10 which connect the heater-cooler unit 2 to the oxygenator 5 and the cardioplegia heat exchanger 6, respectively. The heater-cooler unit 2 includes one or more tanks (not shown) containing temperature-controlled coolant that is provided to the oxygenator 5 and to the cardioplegia heat exchanger 6 via the coolant flow circuit 3 and the cardioplegia coolant circuit 4, respectively. In certain embodiments of this disclosure, the coolant employed in the heating and cooling system 1 is water-based, such as is primarily sterile water, sterile saline or other sterile electrolyte solution. While the term "coolant" is used to describe the heat-conducting fluid flowing within the blood heating and cooling system 1, this fluid may be used to either cool the blood by removing heat energy from the blood or heat the blood by adding heat energy to the blood.

Figure 2:
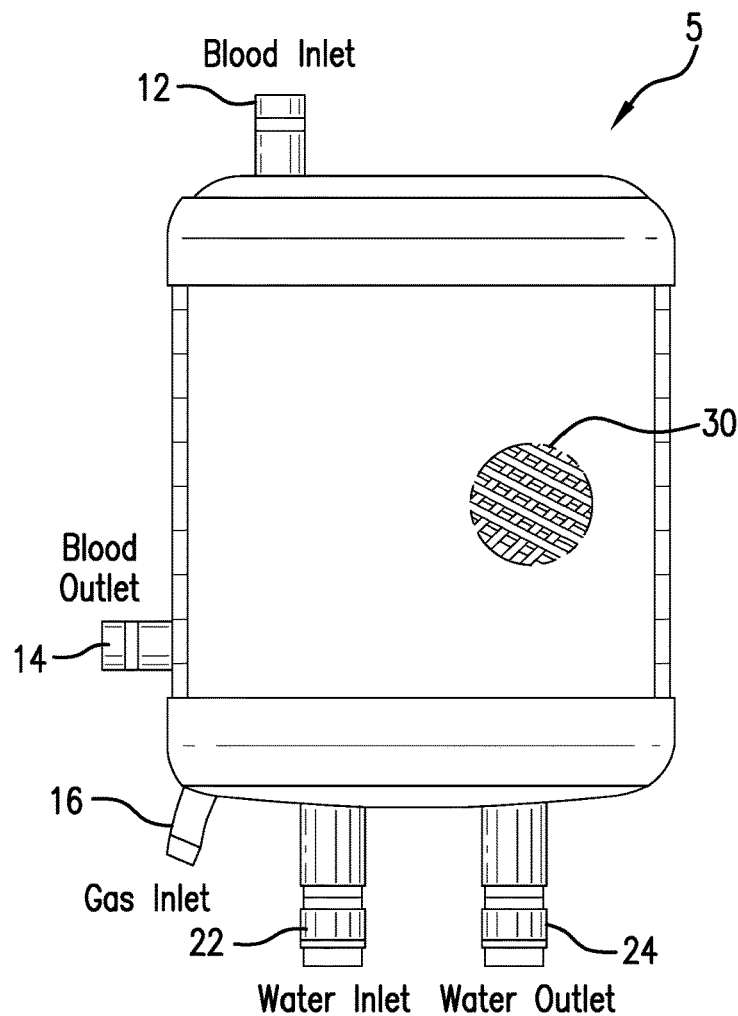
FIG. 2 is a schematic illustration of an oxygenator in accordance with a non-limiting embodiment of the present disclosure.
Figure 3:
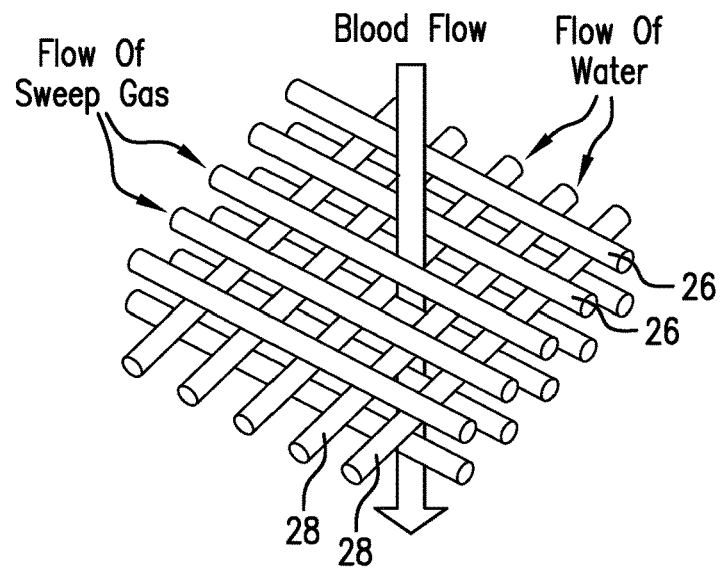
FIG. 3 is a schematic detail view taken about border 30 of FIG. 2, illustrating the structure and arrangement of coolant conduits, sweep gas conduits, and the direction of representative blood flow through one or more passages through the oxygenator of FIG. 2.

FIG. 2 shows details of an oxygenator 5. The oxygenator 5 has a blood inlet 12 in which unoxygenated blood flows into the oxygenator from a blood flow supply, and a blood outlet 14 through which oxygenated blood flows out of the oxygenator and back into the blood flow circuit of the cardiopulmonary bypass system. The oxygenator 5 has a gas inlet 16 in which a sweep gas, such as oxygen or oxygen gas mixture, enters the oxygenator from a sweep gas supply and a gas outlet (not shown) through which sweep gas flows out of the oxygenator and into a sweep gas exhaust circuit of the cardiopulmonary bypass system. The oxygenator 5 has a coolant inlet 22 through which coolant enters the oxygenator from a tube 10 of the heating and cooling system 1, and a coolant outlet 24 through which coolant exits the oxygenator and flows back into another tube 10 of the heating and cooling system 1. As shown in the detail view of FIG. 3 which is taken about border 30 of FIG. 2, sweep gas from the gas inlet 16 flows into a plurality of smaller sweep gas conduits 26 arranged within the walls of the oxygenator and eventually is exhausted through the sweep gas outlet, and coolant from the coolant inlet 22 flows into a plurality of smaller coolant conduits 28 arranged within the walls of the oxygenator and eventually exits the oxygenator through coolant outlet 24. Sweep gas conduits 26 and coolant conduits 28 are arranged at approximately right angles to one another within the oxygenator, and spaces between these conduits 26, 28 provide a network of passages for blood to flow so as to contact the external surfaces of the conduits 26, 28. In this way, oxygen from the sweep gas conduits 26 can diffuse into blood flowing through the network of passages, and coolant flowing through the conduits 28 can be used to control temperature of the blood by adding or removing heat energy from the blood as it flows through the network of passages. As shown in FIG. 3, the flow of blood is substantially at a right angle to the directions of sweep gas flow and coolant flow. In other words, in terms of an imaginary Cartesian coordinate system, the sweep gas flows through the conduits 26 along an x-axis and the coolant flows through the conduits 28 along a y-axis, and the blood flows through the network of passages along a z-axis.

When the heating and cooling system 1 is operating in a coolant mode, blood is flowing through a first extracorporeal blood circuit 7 and a second extracorporeal blood circuit 8, and temperature-controlled coolant, such as a water-based fluid, is flowing through the coolant flow circuit 3 and the cardioplegia coolant circuit 4. The oxygenator 5 contains a first plurality of coolant conduits 28 that form part of the coolant flow circuit 3, and the cardioplegia heat exchanger 6 comprises a second plurality of coolant conduits (not shown) that are part of the cardioplegia coolant circuit 4. The second plurality of coolant conduits of the cardioplegia heat exchanger 6 may be similar to the coolant conduits 28 of the oxygenator 5 in terms of composition, geometry and function and, therefore, for the sake of brevity do not need to be further described or illustrated. The second plurality of coolant conduits of the cardioplegia heat exchanger 6 may be arranged in the same configuration with respect to blood flow as the first plurality of coolant conduits 28 in the oxygenator 5, except that there are no sweep gas conduits in the cardioplegia heat exchanger 6. In the alternative, the heat exchanger 6 may be provided with two sets of coolant conduits 28 arranged at right angles to one another so as to have a similar configuration as the conduits 26 and 28 with respect to blood flow, except that the two sets of conduits in the heat exchanger 6 are two sets of conduits 28 arranged at right angles to one another (i.e., one arranged along the x-axis and the other arranged along the y-axis) with the blood flow directed perpendicularly to both along the z-axis.

Figure 4:
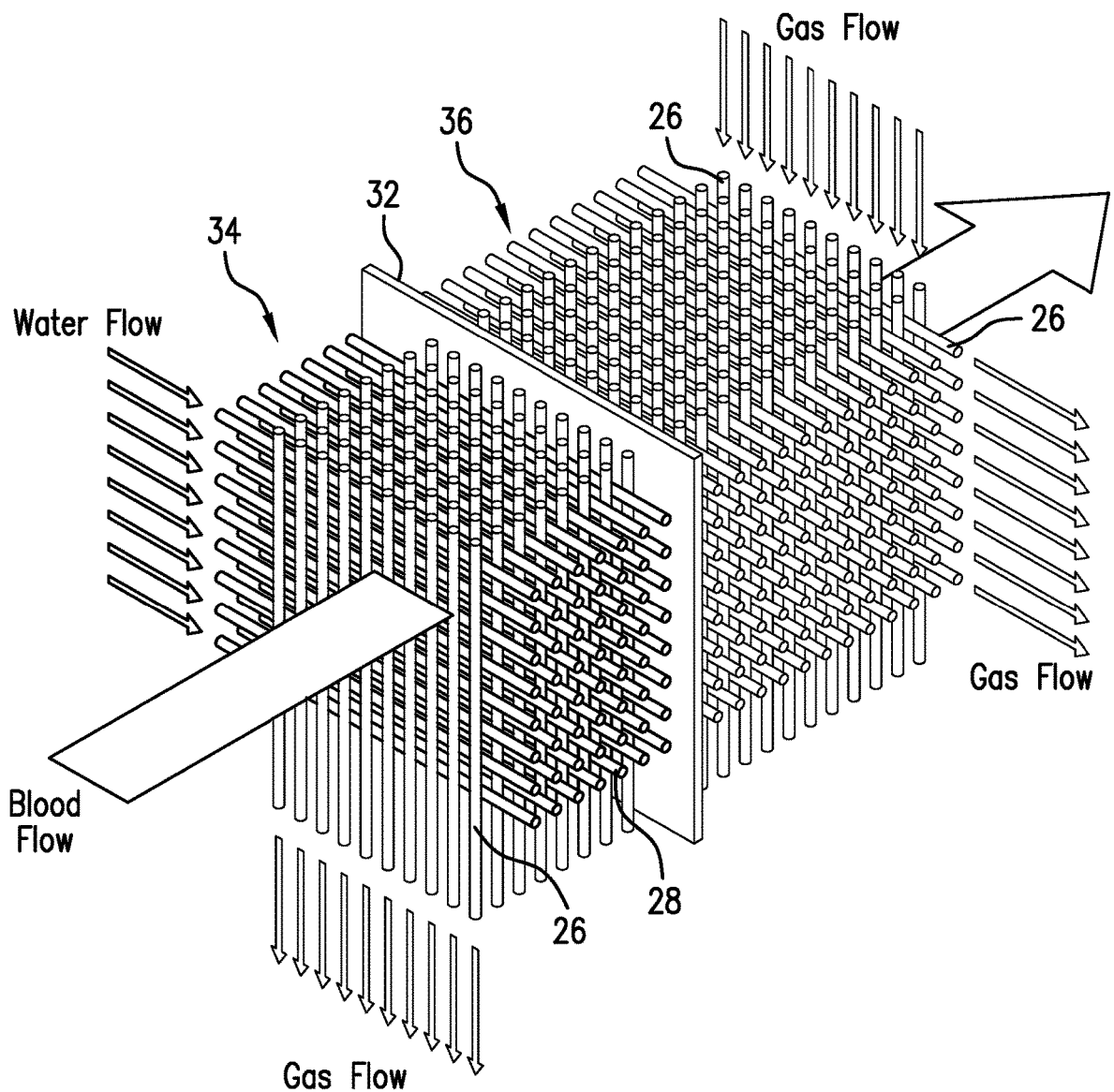
FIG. 4 is a schematic illustration of an oxygenator comprising two regions, in which the arrangement and structure of coolant conduits, sweep gas conduits, and direction of representative blood flow through one or more passages within the two regions of the oxygenator are illustrated.

FIG. 4 illustrates a schematic representation of an oxygenator similar to the schematic of FIG. 3, with a representative partition 32 included to delimit a first section/region 34 from a second section/region 36, in which in the first section 34 has coolant conduits 28 are arranged generally perpendicular to sweep gas conduits 26, and in the second section 36 has sweep gas conduits 36 arranged generally perpendicular to additional sweep gas conduits 26. In such an arrangement, blood flow is directed perpendicular to both the sweep gas conduits 26 and the coolant conduits 28 such that blood flows around the conduits from one side of the oxygenator to the opposite side, passing through the first section 34 prior to the second section 36. Other embodiments in which the blood flow is reversed to first pass through the second section 36 prior to the first section 34 are hereby contemplated but for brevity are not illustrated.

During the coolant mode, blood passing through the first extracorporeal blood circuit 7 contacts an exterior surface of the first plurality of coolant conduits within the oxygenator 5, and heat transfer occurs through the walls of each of the coolant conduits of the first plurality of coolant conduits. Similarly, during the temperature control operating mode, blood passing through the second extracorporeal blood circuit 8 contacts an exterior surface of the second plurality of coolant conduits within the cardioplegia heat exchanger 6, and heat transfer occurs through the walls of each of the coolant conduits of the second plurality of conduits. Thus, the temperature-controlled coolant flows inside the coolant conduits and the blood circulates around the coolant conduits such that heat is dissipated by the temperature-controlled coolant through the walls of the coolant conduits from the blood in order to cool the blood, or heat is added by the temperature-controlled coolant through the walls of the coolant conduits into the blood so as to heat the blood. In this way, the temperature of the blood flowing in the first extracorporeal blood circuit 7 and the second extracorporeal blood circuit 8 is controlled by the heating and cooling system 1.

When the heating and cooling system 1 is operating in a purging mode, temperature-controlled coolant having a trisodium phosphate ($Na_3PO_4$) concentration of about 1-35 millimole/liter is contained within at least one of the coolant flow circuit 3 and the cardioplegia coolant circuit 4. Preferably, the trisodium phosphate (TSP) concentration is about 5-25 millimole/liter, and the trisodium phosphate containing coolant may be water-based. The temperature controlled coolant with trisodium phosphate creates a microbial impeding environment, which is one that impedes microbial activity and interferes with the ability of microbial populations to thrive. That is, the trisodium phosphate concentration is sufficient so the coolant reduces microbial growth and survival, or at least inhibits the reproduction of any bacteria or other microbes within the coolant flow circuit 3, the cardioplegia coolant circuit 4, and/or the heater-cooler unit 2. Preferably, when the heating and cooling system 1 is in the purging mode, the temperature-controlled coolant in the coolant flow circuit 3 and the cardioplegia coolant circuit 4 is maintained at a temperature of greater than about 30° C., and more preferably about 38° C. Non-limiting examples for the temperature of the temperature controlled coolant, such as water or a water-based solution, during the coolant mode or the purging mode include those in the range of 0-40° C. The term "microbe," in accordance with this disclosure includes bacteria, fungi, mycobacteria, and other microorganisms, whether disease producing (pathogens) or not typically disease producing.

When the heating and cooling system 1 is operating in a coolant mode, temperature-controlled coolant having a trisodium phosphate concentration of about 1-10, preferably about 5, millimole/liter is contained within the coolant flow circuit 3 and the cardioplegia coolant circuit 4. Once again, the temperature controlled coolant with trisodium phosphate creates a microbial impeding environment, which is one that impedes microbial activity and interferes with the ability of microbial populations to thrive within the heating and cooling system 1, in this case during the operation of the heating and cooling system 1 in a coolant mode. This operation of the coolant mode of the heating and cooling system 1 should serve to reduce the number of required purging modes for the system that employ coolant possessing a substantially higher trisodium phosphate concentration, as is used during the purging mode. In other words, in accordance with some embodiments of this disclosure, the trisodium phosphate concentration of coolant employed during the purging mode is substantially higher than the trisodium phosphate concentration of coolant employed during coolant mode. In accordance with a non-limiting exemplary embodiment, the concentration of trisodium phosphate in the coolant is about 5 mmol/liter when the heating and cooling system 1 is operating in the continuous coolant mode and the concentration of trisodium phosphate in the coolant is about 25 mmol/liter during the intermittently performed purging mode.

In some embodiments of this disclosure, when the heating and cooling system 1 is in the coolant mode, the coolant flow circuit 3 and the cardioplegia coolant circuit 4 contain temperature-controlled coolant having a pH of 10-13, and more preferably a pH of 11-12. These ranges of an alkaline pH will help create a microbial impeding environment within the temperature controlled coolant provided with trisodium phosphate as part of the coolant composition. In other words, by combining pH environments unfavorable to certain microbes with trisodium phosphate concentrations that are also unfavorable for microbes, the combination of unfavorable pH and trisodium phosphate concentration work together to provide a more effective microbial impeding environment, either in terms of the scope of microbial species that are impeded by the microbial impeding environment and/or in terms of the degree by which a microbial species is impeded by the microbial impeding environment. In accordance with some embodiments of this disclosure, the microbial impeding environment is bacteriostatic and/or fungistatic. In accordance with some embodiments of this disclosure, the microbial impeding environment is bactericidal and/or fungicidal. However, in accordance with this disclosure, a microbial impeding environment need not be either bacteriostatic, fungistatic, bactericidal, or fungicidal, but it must substantially impede microbial activity whether bacterial and/or fungal.

As an additive that maintains the system coolant circuits, plumbing and tubes, trisodium phosphate offers the advantage of being compatible with the materials used in the heating and cooling system 1. When the heating and cooling system 1 is in the coolant mode or the purging mode, the trisodium phosphate in the temperature controlled coolant of the coolant flow circuit 3 and the cardioplegia coolant circuit 4 does not substantially diffuse through the first and second plurality of coolant conduits contained in the oxygenator 5 and the cardioplegia heat exchanger 6, respectively. The first and second plurality of coolant conduits act as a substantial barrier to the diffusion of trisodium phosphate. That is, the first and second plurality of coolant conduits are capable of maintaining a trisodium phosphate concentration ratio across the wall of each such conduit of at least 100:1, from the interior of each conduit (containing the temperature-controlled coolant containing trisodium phosphate) to the exterior of each conduit (which is in contact with blood during the coolant mode). Preferably, the first and second plurality of coolant conduits are capable of maintaining a trisodium phosphate concentration ratio across the wall of each such conduit of at least 1,000:1, and more preferably of at least 10,000:1, from the interior to the exterior of each conduit.

Preferably, the first plurality of coolant conduits and the second plurality of coolant conduits are made of thermoplastic polyurethane membranes configured in a tubular arrangement. An example material of such thermoplastic polyurethane membranes includes ELASTOLLAN™ of BASF Polyurethanes GmbH (Lemförde, Germany). Such thermoplastic polyurethane provides a substantial barrier to the diffusion of trisodium phosphate. That is, the thermoplastic polyurethane is capable of maintaining a trisodium phosphate concentration ratio across the wall of each conduit of at least 100:1, preferably at least 1,000:1, and more preferably at least 10,000:1, from the interior to the exterior of each conduit, as discussed above. However, such thermoplastic polyurethane may allow for the diffusion of hydrogen peroxide therethrough without posing an effective, substantial diffusion barrier.

Also, trisodium phosphate offers the advantage of being an anti-corrosive agent. When used in the heating and cooling system 1, trisodium phosphate included in the coolant composition inhibits the corrosion of the materials of the heating and cooling system 1. While embodiments of the present disclosure may utilize polyurethane materials for the coolant conduits, polypropylene materials may be used for the sweep gas conduits. Desirably, the sweep gas conduits are configured as a microporous hollow fiber tubular conduits.

In accordance with this disclosure, a non-limiting embodiment pertaining to a method of purging an extracorporeal blood heating and cooling system that is connectable to an oxygenator of a cardiopulmonary bypass system is provided. In accordance with this embodiment and with reference to FIG. 1, the method includes the step of adding temperature-controlled coolant to at least one of the coolant flow circuit 3 or the cardioplegia coolant circuit 4, wherein the temperature-controlled coolant has a trisodium phosphate concentration of 1-35 millimole/liter. Preferably, the trisodium phosphate concentration is 5-25 millimole/liter. The coolant may be primarily water-based in accordance with some embodiments of this disclosure.

This method further includes the step of subsequently flowing the temperature-controlled coolant within the coolant flow circuit and/or the cardioplegia coolant circuit in a manner that at least inhibits the growth of microbes within the respective circuit(s). As discussed above, the temperature controlled coolant with trisodium phosphate creates a microbial impeding environment, and at least inhibits the reproduction of existing bacteria or microbes within the coolant flow circuit 3 and/or the cardioplegia coolant circuit 4. Preferably, the temperature-controlled coolant in the coolant flow circuit 3 and the cardioplegia coolant circuit 4 is maintained at a temperature greater than about 30° C., more preferably about 38° C. Non-limiting examples for the temperature of the temperature controlled water during this method include those in the range of 0-40° C.

In accordance with this method, the first and second plurality of coolant conduits act as a substantial barrier to the diffusion of trisodium phosphate. That is, the first and second plurality of coolant conduits are capable of maintaining a trisodium phosphate concentration ratio across the wall of each such conduit of at least 100:1, from the interior of each conduit (containing the temperature-controlled water containing trisodium phosphate) to the exterior of each conduit. Preferably, the first and second plurality of coolant conduits are capable of maintaining a trisodium phosphate concentration ratio across the wall of each such conduit of at least 1,000:1, and more preferably of at least 10,000:1, from the interior to the exterior of each coolant conduit. Preferably, the first plurality of coolant conduits and the second plurality of coolant conduits are made of thermoplastic polyurethane.

In accordance with this disclosure, a non-limiting embodiment pertaining to a method of operating an extracorporeal blood heating and cooling system that is connectable to an oxygenator of a cardiopulmonary bypass system is provided. In accordance with this embodiment and with reference to FIG. 1, the method includes the step of adding temperature-controlled coolant to the coolant flow circuit 3 and the cardioplegia coolant circuit 4, wherein the temperature-controlled coolant has a trisodium phosphate concentration of 1-10 millimole/liter and a pH of 10-13. Preferably, the temperature-controlled coolant has a trisodium phosphate concentration of about 5 millimole/liter and a pH of about 11-12. The temperature-controlled coolant may, in accordance with some embodiments, be primarily a water-based composition.

This method further includes the step of subsequently flowing the temperature-controlled coolant through the coolant flow circuit 3 and the cardioplegia coolant circuit 4 in order to at least inhibit the growth of microbes within the coolant flow circuit 3 and the cardioplegia coolant circuit 4. As discussed above, the temperature controlled coolant with trisodium phosphate creates a microbial impeding environment, and at least inhibits the reproduction of any bacteria and/or other microbes existing within the coolant flow circuit 3 and/or the cardioplegia coolant circuit 4. Preferably, the temperature-controlled coolant in the coolant flow circuit 3 and the cardioplegia coolant circuit 4 is at a temperature greater than about 30° C., more preferably about 38° C. Non-limiting examples for the temperature of the temperature controlled coolant during this method include those in the range of 0-40° C.

In accordance with this method, the first and second plurality of coolant conduits act as a substantial barrier to the diffusion of trisodium phosphate. That is, the first and second plurality of coolant conduits are capable of maintaining a trisodium phosphate concentration ratio across the wall of each such conduit of at least 100:1, from the interior of each conduit (containing the temperature-controlled coolant containing trisodium phosphate) to the exterior of each coolant conduit. Preferably, the first and second plurality of coolant conduits are capable of maintaining a trisodium phosphate concentration ratio across the wall of each such conduit of at least 1,000:1, and more preferably of at least 10,000:1, from the interior to the exterior of each coolant conduit. Such walls may for example have an average wall thickness of about 70 μm (micrometers). Preferably, the first plurality of coolant conduits and the second plurality of coolant conduits are made of a thermoplastic polyurethane that does not provide a substantial diffusion barrier to hydrogen peroxide.

Testing Results

In accordance with this disclosure, several non-limiting embodiments pertaining to a method of purging an extracorporeal blood heating and cooling system that is connectable to an oxygenator of a cardiopulmonary bypass system are exemplified as follows.

Sixty oxygenators were connected to heater-cooler units with standard tubing. The oxygenators contained thermoplastic polyurethane cooling conduits that formed part of the coolant flow circuit. The blood circuit of the oxygenators were filled with 0.9% isotonic saline solution that was used as a blood replacement, and the coolant flow circuit was filled with temperature-controlled water containing trisodium phosphate. There was one trisodium phosphate concentration of 1 mmol/l, one at 10 mmol/l, and the remainder at 5 mmol/l. The heater-cooler units were initially operated at a minimum temperature setting of 10° C., 3° C. or 1° C. for one hour, and then operated for five hours at a maximum temperature setting of about 40° C. to simulate a surgical use including rapid cooling. The heater-cooler units were then again operated at a minimum temperature setting of 10° C., 3° C. or 1° C. for one hour, followed by seventeen hours at a maximum temperature setting, at which point the testing was concluded at 24 hours, and phosphate measurements were taken in the isotonic saline solution and the temperature-controlled water containing trisodium phosphate.

All of the phosphate measurements taken showed a concentration ratio of well above 100:1 (temperature-controlled water containing trisodium phosphate concentration:isotonic saline solution concentration), and most were above 1,000:1 and 10,000:1. Thus, the testing showed that the thermoplastic polyurethane of the coolant conduits in the oxygenators provided a substantial barrier to the diffusion of trisodium phosphate across the conduit walls. However, in a different series of tests employing hydrogen peroxide as an additive to the coolant instead of trisodium phosphate, it was found that the thermoplastic polyurethane of the coolant conduits did not provide a substantial barrier to diffusion of the hydrogen peroxide across the conduit walls.

While the present disclosure provides multiple exemplary embodiments, it will be understood by those skilled in the art that various changes may be made and equivalents may be substituted for elements thereof without departing from the scope of this disclosure. In addition, many modifications may be made to adapt a particular situation or material to the teachings of this disclosure without departing from the essential scope thereof. Therefore, it is intended that the invention, as defined in the appended claims, not be limited to any particular embodiment disclosed herein, but that the invention will include all embodiments falling within the scope of the claims. Also, in the drawings and the description, there have been disclosed exemplary embodiments and, although specific terms may have been employed, they are unless otherwise stated used in a generic and descriptive sense only and not for purposes of limitation. Moreover, the use of the terms first, second, etc. do not denote any order or importance, but rather the terms first, second, etc. are used to distinguish one element from another. Furthermore, the use of the terms a, an, etc. do not denote a limitation of quantity, but rather denote the presence of at least one of the referenced item unless otherwise explicitly indicated. In addition, unless otherwise indicated, use of the term "about" shall indicate a range of ±10%.

I claim:

1. An extracorporeal blood heating and cooling system that is connectable to an oxygenator of a cardiopulmonary bypass system, the heating and cooling system comprising:
   a heater-cooler unit;
   a coolant flow circuit that is configured to pass coolant through the heater-cooler unit and the oxygenator; and
   a cardioplegia coolant circuit that is configured to pass coolant through the heater-cooler unit and a cardioplegia heat exchanger;
   wherein the oxygenator comprises a first plurality of coolant conduits that form part of the coolant flow circuit, and wherein when the heating and cooling system is in a coolant mode, blood passing through a first extracorporeal blood circuit contacts an exterior surface of the first plurality of coolant conduits;
   wherein the cardioplegia heat exchanger comprises a second plurality of coolant conduits that are part of the cardioplegia coolant circuit, and wherein when the heating and cooling system is in the coolant mode, blood passing through a second extracorporeal blood circuit contacts an exterior surface of the second plurality of coolant conduits;
   wherein when the heating and cooling system is in a purging mode, the coolant flow circuit and the cardioplegia coolant circuit contain temperature-controlled coolant having a trisodium phosphate concentration of about 1-35 millimole/liter;
   wherein when the heating and cooling system is in the coolant mode, the coolant flow circuit and the cardioplegia coolant circuit contain temperature-controlled water having a trisodium phosphate concentration of about 1-10 millimole/liter; and
   wherein when the heating and cooling system is in the coolant mode or the purging mode, the first and second plurality of coolant conduits are capable of maintaining a trisodium phosphate concentration ratio across the wall of each coolant conduit of at least 100:1, from the interior to the exterior of each coolant conduit.

2. The heating and cooling system of claim 1, wherein the trisodium phosphate concentration ratio across the wall of each coolant conduit is at least 1,000:1.

3. The heating and cooling system of claim 1, wherein the trisodium phosphate concentration ratio across the wall of each coolant conduit is at least 10,000:1.

4. The heating and cooling system of claim 1, wherein when the heating and cooling system is in the purging mode, the coolant flow circuit and the cardioplegia coolant circuit contain temperature-controlled water having a trisodium phosphate concentration of about 5-25 millimole/liter.

5. The heating and cooling system of claim 1, wherein when the heating and cooling system is in the coolant mode, the coolant flow circuit and the cardioplegia coolant circuit contain temperature-controlled water having a pH of 10-13.

6. The heating and cooling system of claim 1, wherein when the heating and cooling system is in the coolant mode, the coolant flow circuit and the cardioplegia coolant circuit contain temperature-controlled water having a pH of 11-12.

7. The heating and cooling system of claim 1, wherein when the heating and cooling system is in the purging mode, the coolant flow circuit and the cardioplegia coolant circuit contain temperature-controlled water at a temperature greater than about 30° C.

8. The heating and cooling system of claim 1, wherein the first plurality of coolant conduits and the second plurality of coolant conduits comprise thermoplastic polyurethane.

9. A method of purging an extracorporeal blood heating and cooling system that is connectable to an oxygenator of a cardiopulmonary bypass system, the heating and cooling system comprising: a heater-cooler unit; a coolant flow circuit that is configured to pass temperature-controlled coolant through the heater-cooler unit and an oxygenator; and a cardioplegia coolant circuit that is configured to pass temperature-controlled coolant through the heater-cooler unit and a cardioplegia heat exchanger; wherein the oxygenator comprises a first plurality of coolant conduits that form part of the coolant flow circuit when the oxygenator is connected to the heating and cooling system, and wherein when the heating and cooling system is in a coolant mode, blood passing through a first extracorporeal blood circuit contacts an exterior surface of the first plurality of coolant conduits; and wherein the cardioplegia heat exchanger comprises a second plurality of coolant conduits that are part of the cardioplegia coolant circuit, and wherein when the heating and cooling system is in the coolant mode, blood passing through a second extracorporeal blood circuit contacts an exterior surface of the second plurality of coolant conduits; the method comprising the steps of:
   adding temperature-controlled coolant to at least one of the coolant flow circuit or the cardioplegia coolant circuit, wherein the temperature-controlled coolant has a trisodium phosphate concentration of about 1-35 millimole/liter; and
   subsequently flowing the temperature-controlled coolant within the at least one of the coolant flow circuit or the cardioplegia coolant circuit in a manner that at least inhibits growth of microbes within the at least one of the coolant flow circuit or the cardioplegia coolant circuit;
   wherein the first and second plurality of coolant conduits are capable of maintaining a trisodium phosphate concentration ratio across the wall of each coolant conduit of at least 100:1, from the interior to the exterior of each coolant conduit.

10. The method of claim 9, wherein the trisodium phosphate concentration ratio across the wall of each coolant conduit is at least 1,000:1.

11. The method of claim 9, wherein the trisodium phosphate concentration ratio across the wall of each coolant conduit is at least 10,000:1.

12. The method of claim 9, wherein temperature-controlled water is added to both the coolant flow circuit and the cardioplegia coolant circuit.

13. The method of claim 12, wherein the temperature-controlled water has a trisodium phosphate concentration of 5-25 millimole/liter.

14. The method of claim 13, wherein the temperature-controlled water is at a temperature greater than about 30° C.

15. The method of claim 9, wherein the first plurality of coolant conduits and the second plurality of coolant conduits comprise thermoplastic polyurethane.

16. The method of claim 9, wherein the trisodium phosphate of the coolant inhibits corrosion of the heating and cooling system.

17. A method of operating an extracorporeal blood heating and cooling system, wherein the heating and cooling system is connectable to an oxygenator of a cardiopulmonary bypass system, the heating and cooling system comprising: a heater-cooler unit; a coolant flow circuit that is configured to pass temperature-controlled coolant through the heater-cooler unit and the oxygenator; and a cardioplegia coolant circuit that is configured to pass temperature-controlled coolant through the heater-cooler unit and a cardioplegia heat exchanger; wherein the oxygenator comprises a first plurality of coolant conduits that form part of the coolant flow circuit when the heating and cooling system is connected to the oxygenator, and wherein when the heating and cooling system is operating in a coolant mode, blood passing through a first extracorporeal blood circuit contacts an exterior surface of the first plurality of coolant conduits; and wherein the cardioplegia heat exchanger comprises a second plurality of coolant conduits that are part of the cardioplegia coolant circuit, and wherein when the heating and cooling system is operating in the coolant mode, blood passing through a second extracorporeal blood circuit contacts an exterior surface of the second plurality of coolant conduits; the method comprising the steps of:

adding temperature-controlled coolant to the coolant flow circuit and the cardioplegia coolant circuit, wherein the temperature-controlled coolant is water-based and has a trisodium phosphate concentration of 1-10 millimole/liter and a pH of 10-13; and subsequently flowing the temperature-controlled coolant through the coolant flow circuit and the cardioplegia circuit in order to at least inhibit growth of microbes within the coolant flow circuit and the cardioplegia circuit;

wherein the first and second plurality of coolant conduits are capable of maintaining a trisodium phosphate concentration ratio across the wall of each coolant conduit of at least 100:1, from the interior to the exterior of each coolant conduit.

18. The method of claim 17, wherein the trisodium phosphate concentration ratio across the wall of each coolant conduit is at least 1,000:1.

19. The method of claim 17, wherein the trisodium phosphate concentration ratio across the wall of each coolant conduit is at least 10,000:1.

20. The method of claim 17, wherein the temperature-controlled coolant has a pH of 11-12.

21. The method of claim 17, wherein the temperature-controlled coolant is maintained at a temperature greater than about 30° C.

22. The method of claim 17, wherein the first plurality of coolant conduits and the second plurality of coolant conduits comprise thermoplastic polyurethane.

23. The method of claim 17, wherein the trisodium phosphate inhibits corrosion of the heating and cooling system.

24. The method of claim 22, wherein walls of the first plurality of coolant conduits and walls of the second plurality of coolant conduits are made of the thermoplastic polyurethane and do not provide a barrier to diffusion of hydrogen peroxide across these walls.

* * * * *